United States Patent
Chen et al.

(10) Patent No.: US 9,943,615 B2
(45) Date of Patent: Apr. 17, 2018

(54) NANOPARTICLES AND METHOD FOR MANUFACTURING THE SAME

(71) Applicant: Institute of Nuclear Energy Research, Atomic Energy Council, Executive Yuan, R.O.C., Taoyuan (TW)

(72) Inventors: Su-Jung Chen, Taoyuan County (TW); Chang-An Chen, Taoyuan County (TW); Chung-Yen Li, Taoyuan County (TW); Chu-Nian Cheng, Taoyuan County (TW); Ming-Syuan Lin, Taoyuan County (TW); Shu-Pei Chiu, Taoyuan County (TW); Chih-Hsien Chang, Hsinchu (TW)

(73) Assignee: INSTITUTE OF NUCLEAR ENERGY RESEARCH ATOMIC ENERGY COUNCIL, EXECUTIVE YUAN R.O.C, Taoyuan (TW)

( * ) Notice: Subject to any disclaimer, the term of this patent is extended or adjusted under 35 U.S.C. 154(b) by 182 days.

(21) Appl. No.: 14/940,714

(22) Filed: Nov. 13, 2015

(65) Prior Publication Data
US 2017/0119914 A1 May 4, 2017

(30) Foreign Application Priority Data
Oct. 29, 2015 (TW) .............................. 104135637 A

(51) Int. Cl.
A61K 51/08 (2006.01)
A61K 51/12 (2006.01)

(52) U.S. Cl.
CPC .......... *A61K 51/081* (2013.01); *A61K 51/088* (2013.01); *A61K 51/1244* (2013.01)

(58) Field of Classification Search
None
See application file for complete search history.

(56) References Cited

U.S. PATENT DOCUMENTS

2009/0304720 A1* 12/2009 Kreuter ................ A61K 31/451
424/179.1
2015/0023912 A1* 1/2015 Kratz ............... A61K 47/48284
424/85.2

OTHER PUBLICATIONS

Langer et al., "Optimization of the preparation process for human serum albumin (HSA) nanoparticles", International Journal of Pharmaceutics 257: 169-180 (2003). (Year: 2003).*
B. von Storp et al.,"Albumin nanoparticles with predictable size by desolvation procedure", Journal of Microencapsulation 29:2, 138-146 (2012) (Year: 2012).*
Kouchakzadeh et al.,"Efficient loading and entrapment of tamoxifen in human serum albumin based nanoparticulate delivery system by a modified desolvation technique", Chemical Engineering Research and Design 92: 1681-1692 (2014) (Year: 2014).*

* cited by examiner

*Primary Examiner* — Anand U Desai
(74) *Attorney, Agent, or Firm* — Locke Lord LLP; Tim Tingkang Xia, Esq.

(57) ABSTRACT

Disclosed herein are nanoparticles and method for manufacturing the same. The nanoparticle is essentially composed of albumin and polyethylene glycol, wherein the albumin is covalently crosslinked with the polyethylene glycol.

2 Claims, 3 Drawing Sheets

NANOPARTICLES AND METHOD FOR MANUFACTURING THE SAME

CROSS REFERENCE TO RELATED APPLICATION

The present application is based on, and claims priority from, Taiwan Application Serial Number 104135637, filed on Oct. 29, 2015, the disclosure of which is hereby incorporated by reference herein in its entirety.

TECHNICAL FIELD

The present invention relates to a nanoparticle and a method for manufacturing the same, and more particularly to a nanoparticle that uses human serum albumin (HSA).

BACKGROUND

HSA is essentially synthesized by the liver, and is an important material transport carrier in the blood, and based on the characteristic that it has no obvious immunogenicity, the HSA can be used as carrier protein that improves the half life of drugs.

In applications of the prior art, the HSA can be used along with small molecule drugs, to serve as a carrier that transports and releases drugs. Binding of the HSA and the small molecule drugs can increase solubility of the drugs in plasma, reduce toxicity and avoid oxidization, thereby increasing the half life of treatment of the small molecule drugs in the body of an individual. However, too strong binding of the HSA and the small molecule drugs may also affect release effects in target tissues of the drugs.

The prior art, in order to improve the defects of the HSA carrier, further prepares the albumin into nanoparticles through a nanotechnology, to make it have better stability, longer storage life and a wider range of applications. The advantage of preparing the albumin into nanoparticles lies in that it can encapsulate and transfer cancer drugs with low solubility. For example, at present, an albumin bonding Abraxane nanoparticle (Abraxane®) has existed, and the average particle size of the nanoparticle is about 130 nm. The US FDA approved in 2006 that Abraxane® can be applied to metastatic breast cancer patients ineffective or relapsed for other therapeutic drugs, and in 2012, the US FDA approved once again that the drug can be applied to treatment of patients with non-small cell lung cancer. The albumin nanoparticle can accumulate drugs to tumor sites by means of Enhanced Permeability and Retention effect. At the same time, the particle can be transferred to the tumor by means of a 60 kDa glycoprotein (gp60) receptor (albondin) with selective over-expression. In addition, it is pointed out according to the study that the albumin nanoparticle can carry out transcytosis by means of receptors in cancer cells, and is bonded to secreted protein acidic rich in cysteine (SPARC) on the surface of cancerous cells. Based on the aforementioned three mechanisms of action, Abraxane® has lower toxicity compared with the traditional chemotherapy drug Taxol and can shorten drug administration time and have better therapeutic effects. However, stability of such an albumin nanoparticle is not good, and stability can only be maintained for 2-8 hours when the albumin nanoparticle is dispersed in a 0.9% sodium chloride solution, which still has limitations to clinical applications.

In addition, it should be noted that in current manufacturing of albumin nanoparticles identical with or similar to Abraxane®, during preparation, poisonous substances such as trichloromethane or dichloromethane may be used, the preparation procedure is tedious and spends a lot of time, thus increasing the cost of production, and the nanoparticle made with such steps has a potential risk of being contaminated with toxic substances.

In view of this, there is an urgent need for an improved nanoparticle and a method for manufacturing the same in the field, so as to improve the shortcomings of the prior art.

SUMMARY

In order to make readers understand the basic meaning of the disclosure, the summary provides a brief description about the disclosure. Moreover, the summary is not a complete description about the disclosure, and is not intended to define the technical features or claims of the present invention.

To solve the aforementioned problems, one aspect of the disclosure relates to a nanoparticle. The nanoparticle is essentially composed of albumin and polyethylene glycol, wherein the albumin is covalently crosslinked with the polyethylene glycol.

According to another embodiment of the disclosure, the nanoparticle of the disclosure further comprises a radioactive material, disposed on a surface of the nanoparticle. In any optional embodiment, the radioactive material is rhenium-188 or technetium-99 m.

In a specific embodiment, the albumin is human serum albumin.

In a preferred embodiment, the polyethylene glycol of the nanoparticle has a maleimide functional group.

Another aspect of the disclosure relates to a method for manufacturing a nanoparticle, comprising:
a) dissolving human serum albumin and polyethylene glycol in a PBS solution, to obtain a mixture;
b) dissolving the mixture to a saline solution, and adding 0.05-0.2 N of sodium hydroxide;
c) adding a methanol/ethanol mixture for reaction;
d) after precipitation of the albumin, adding a glutaraldehyde water solution for reaction; and
e) obtaining the nanoparticle through ultracentrifugation.

In one embodiment, centrifugation is carried out after step a) reacts for 20 hours.

In another embodiment, step b) is completed to filter to obtain a filtering medium, and then step c) is performed.

In a particular embodiment, centrifugation is carried out after step d) reacts for 12 hours.

According to a preferred embodiment of the disclosure, the method further comprises adding the nanoparticle to a trhenium-188 solution, filling the trhenium-188 solution with nitrogen and then carrying out a reaction, to obtain a nanoparticle that marks trhenium-188.

After referring to the examples hereinafter, those of ordinary skill in the art can fully understand the central concept, the technical means adopted and various implementation aspects of the present invention.

BRIEF DESCRIPTION OF DRAWINGS

To make the aforementioned and other objectives, features, advantages and examples of the present invention more comprehensible, the description of the drawings is as follows.

DETAILED DESCRIPTION OF DISCLOSED EMBODIMENTS

Figure 1A:
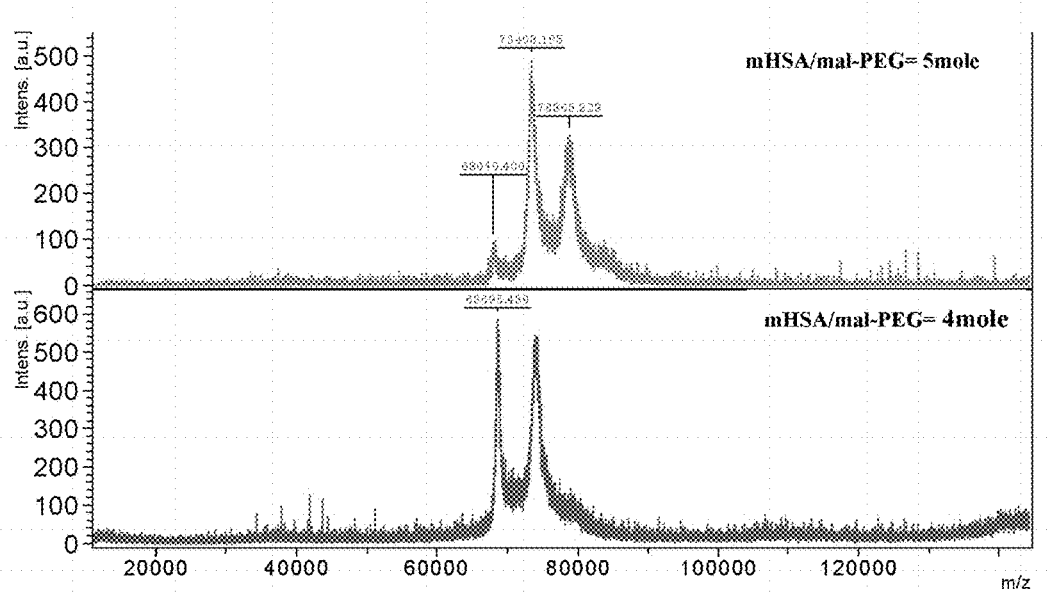
FIG. 1A shows results of mass spectrometry analysis on polyethylene glycol (PEG)-HSA (denoted by HSA/mal-PEG in the figure) of the present invention according to one embodiment of the present invention.

To make statement of the disclosure more detailed and complete, illustrative literal statement is put forward hereinafter for implementation aspects and specific examples of the present invention; however, the implementation aspects and specific examples of the present invention are not merely limited thereto.

Unless otherwise specified, meanings of scientific and technical terms used in the specification are the same as those understood and commonly used by those of ordinary skill in the art. Moreover, the nouns used in the specification all cover singular and plural forms of the nouns, unless other indicated.

As stated in the specification, the word "about" usually means that an actual value is within 10%, 5%, 1% or 0.5% of a particular value or range. The word "about" herein represents that an actual value falls within an acceptable standard error of an average value, which depends on consideration of those of ordinary skill in the art. Except experiments, or unless otherwise explicitly specified, it should be understood that the range, number, value and percentage used herein are all modified by "about". Therefore, unless otherwise specified, values or parameters disclosed in the specification and the appended claims are all approximate values, and may vary as required.

The present invention proposes a new nanoparticle, which can improve the problem of poor stability of the albumin nanoparticle. On the other hand, the present invention proposes a method for manufacturing a nanoparticle, so that the nanoparticle of the present invention can be obtained without using poisonous substances such as trichloromethane or dichloromethane during manufacturing the albumin nanoparticle, that is, the past tedious manufacturing process is simplified, to achieve the aim of enhancing the efficiency of manufacturing the albumin nanoparticle and reducing the risk that the nanoparticle is contaminated by highly toxic chemicals. In addition, the present invention further proposes a new method for manufacturing a nanoparticle marked with a radioactive material, and the method is different from the prior art in that it can be completed without a dispersing agent and a stabilizer.

The nanoparticle of the present invention, structurally, is essentially composed of albumin and polyethylene glycol, wherein the albumin is covalently crosslinked with the polyethylene glycol. In one embodiment, the nanoparticle of the present invention can serve as a carrier, to transfer a preparation to a target area. The preparation may be a therapeutic agent or a developing agent, wherein the therapeutic agent is a chemotherapy drug or a radiotherapy drug. In any optional embodiment, the chemotherapy drug may be a liposoluble chemotherapy drug or a non-liposoluble chemotherapy drug, and those of ordinary skill in the art can select a suitable effective chemotherapy drug according to actual use conditions, for example, Taxol, erlotinib, gefitinib and the like.

In one preferred embodiment, the nanoparticle of the present invention may be combined with the radiotherapy drug, to serve as a radioactive isotopic carrier. The advantages of the nanoparticle with a radioactive material of the present invention are as follows: (1) the nanoparticle has biodegradability and biocompatibility, which eliminates security concerns remaining in the body; and (2) the nanoparticle can carry out a marking reaction in high-temperature environments, which facilitates radioactive nuclide marking.

In any optional embodiment, the radiotherapy drug or radioactive material may be rhenium-188 or technetium-99 m.

In addition, the specific steps of the manufacturing method of the present invention are as follows:

a) dissolving human serum albumin and polyethylene glycol in a PBS solution, to obtain a mixture;

b) dissolving the mixture to a saline solution, and adding 0.05-0.2 N of sodium hydroxide;

c) adding a methanol/ethanol mixture for reaction;

d) after precipitation of the albumin, adding a glutaraldehyde water solution for reaction; and e) obtaining the nanoparticle through ultracentrifugation.

In one embodiment of the present invention, a mal ratio of HSA to PFG in step a) is about 1:2 to 1:10, for example, about 1:1, 1:2, 1:3, 1:4, 1:5, 1:6, 1:7, 1:8, 1:9 and 1:10. In one preferred embodiment, the mal ratio is about 1:3 to 1:6; in one more preferred embodiment, the mal ratio is about 1:5.

In any optional embodiment, molecular weight of the PEG used in the present invention is 2000-5000 Da.

In another specific embodiment of the present invention, in step a), the HSA and the PFG are dissolved in an about 5-20 mM PBS solution, and in one preferred embodiment, the PBS solution is 10 mM PBS.

In a non-limited implementation, centrifugation is carried out after step a) goes on for a reaction time. In any optional embodiment, the reaction time is 10-40 hours, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 hours; in one preferred embodiment, the particular time is 15-30 hours; in one more preferred embodiment, the reaction time is 15-25 hours.

According to a non-limited implementation of the present invention, after completion of step b), filtering is performed to obtain a filtering medium, and then step c) and steps after step c) are performed.

In another implementation, centrifugation is carried out after step d) goes on for a reaction time. In any optional embodiment, the reaction time is 5-30 hours, for example, 5, 6, 7, 8, 9, 10, 11, 12, 13, 14, 15, 16, 17, 18, 19, 20, 21, 22, 23, 24, 25, 26, 27, 28, 29 or 30 hours; in one preferred embodiment, the particular time is 5-20 hours; in one more preferred embodiment, the reaction time is 10-15 hours.

According to a specific embodiment of the present invention, step a) reacts for 20 hours, and step d) reacts for 12 hours.

Moreover, in step c) of the present invention, the methanol and ethanol mixture is mixed according to a proportion of a weight ratio of about 7:3. In another embodiment, the methanol and ethanol mixture is mixed according to a proportion of a weight ratio of about 8:2, and in a further embodiment, the methanol and ethanol mixture is mixed according to a proportion of a weight ratio of about 6:4.

According to another embodiment of the present invention, the manufacturing method of the present invention further comprises marking a radioactive material on a surface of the nanoparticle. In a specific embodiment, the nanoparticle is added to a solution containing a radioactive material, and then the solution is filled with nitrogen for a reaction, to obtain a nanoparticle of a marked trhenium-188. It should be noted that, in the process of marking the radioactive material with the manufacturing method of the present invention, it is not necessary to use any interfacial agent as a dispersing agent or to add any stabilizer, which simplifies the conventional manufacturing procedure and significantly increases production efficiency. The nanoparticle with a radioactive material of the present invention, in addition to treating the cancer as a radioactive drug, can also diagnose diseases as a developing agent.

In any optional embodiment, the particle size of the nanoparticle of the present invention is about 1-10 nm; in one preferred embodiment, the particle size of the nanoparticle of the present invention is about 20-80 nm; and in one more preferred embodiment, the particle size of the nanoparticle of the present invention is about 50-75 nm.

Several embodiments are disclosed hereinafter to elaborate various different implementation aspects of the present invention, to enable those of ordinary skill in the art can implement the technical contents of the present invention according to the disclosure of the specification. Therefore, various embodiments disclosed hereinafter cannot be used to limit the claims of the present invention. Moreover, all documents cited in the specification can be regarded as complete reference and a part of the specification.

Example 1 Manufacturing of PEG-HSA 316 mg of HSA and 120 mg of mal-PEG5000 (the mal ratio is 1:5) were dissolved in a 10 mM PBS solution, and reacted for 20 hours at 37° C., and after reaction, the solution was moved into an Amico Ultra-15 (50 KD) centrifuge tube, which was centrifuged for 30 minutes at a rotating speed of 4400 rpm. After centrifugation, the lower solution was removed, then 10 ml of pure water was injected to the top of the centrifuge tube, the process was repeated three times, and finally the upper solution was taken out for freeze-drying, to obtain a 254 mg sample containing mPEG-HSA.

Figure 1B:
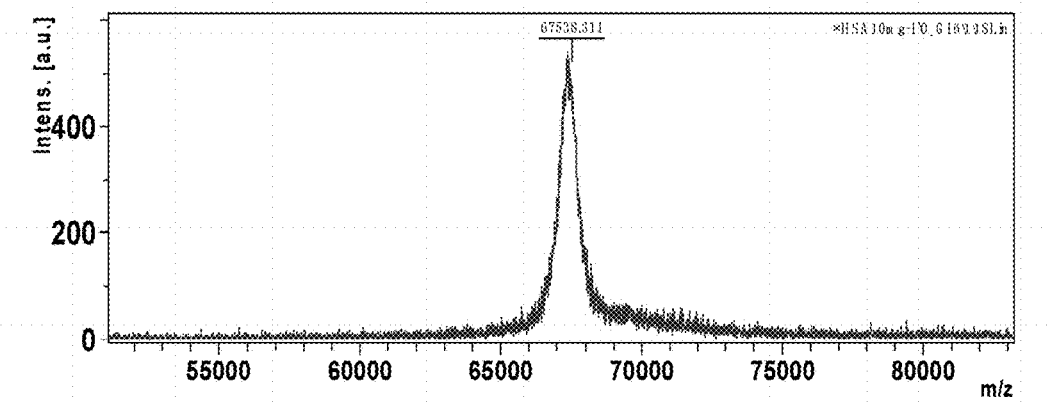
FIG. 1B shows results of mass spectrometry analysis on HSA according to one embodiment of the present invention.

The sample containing mPEG-HSA carried out sampling analysis with a HPLC system (a reaction condition was: RP-18 tubular column, moving phase A: 100% water 75-40% moving phase B: ACN100%+0.01% TFA 50 minutes) and sample concentration of 5 mg/ml, and retention time of mPEG-HSA was 22.51 minutes. A sample coupling rate >70% can be obtained. It can be obtained according to mass spectrum analysis that molecular weight of mPEG-HSA was about 72 Kd, and reference can be made to FIG. 1A and FIG. 1B for results.

Example 2 Manufacturing of PEG-HSA Nanoparticle

Figure 2:
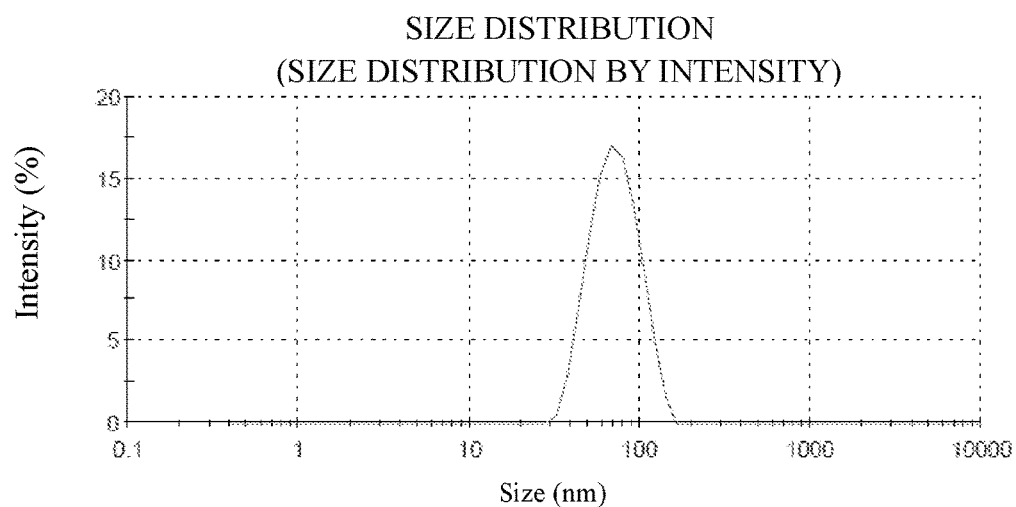
FIG. 2 is a graph showing the particle size distribution by intensity of the PEG-HSA nanoparticle according to another embodiment of the present invention.

The PEG-HSA nanoparticle manufactured according to Example 1 was used to manufacture a nanoparticle, 100 mg of PEG-HSA was dissolved in a 10 mM 0.9% salt solution, after complete dissolution, a 100 uL 0.1 N sodium hydroxide solution was added slowly, and then 0.22 um filter paper was used for filtering. The filtered solution was added to a 4 ml of a methanol and ethanol mixture (a weight ratio of 7:3) through peristaltic pump, which reacted at room temperature at a rotating speed of 700 rpm. After precipitation of albumin particles, a 58.8 microliters of 8% glutaraldehyde water solution (at a rotating speed of 700 rpm) was added slowly, then the rotating speed was reduced to 300 rpm, and the reaction went on for 12 hours. The solution after reaction was moved into the centrifuge tube and was centrifuged (30000 g, centrifuged for 30 minutes) with an ultra-high-speed vacuum centrifuge, after centrifugation, liquid supernatant was removed, after 1 ml of pure water was added to disperse sediments, centrifugation (30000 g, centrifuged for 30 minutes) was performed with a high-speed vacuum centrifuge, the process was repeated three times, to obtain a liquid suspension containing the nanoparticle of the present invention, and after analysis with a particle size analyzer, the particle size of the nanoparticle was 67.2 nm and surface potential was −25.1 mV, wherein results of the particle size were shown in FIG. 2.

Example 3 Manufacturing of the Nanoparticle of a Marked Radioactive Material of the Present Invention In this example, the present invention selected rhenium-188 to manufacture a nanoparticle with a radioactive material. Radioactive nuclide rhenium-188 was a radioisotope with diagnosis and treatment functions, which had a moderate half life (16.9 hours) and can emit 155000 electron volts (keV) gamma rays suitable for applications to nuclear medical imaging diagnosis, and the beta energy released was up to 2.12 million electron volts (MeV), suitable for applications to nuclear medical cancer treatment.

Specific steps of the example were as follows:

A 5 mg of PEG-HSA nanoparticle was dissolved in a 500 microliters of 0.9% sodium chloride solution. A 150 microliters of stannous chloride solution (10 mg/ml in a 1 N hydrochloric acid solution) was added; and a 500 microliters of citric acid solution (40 g/ml) was added. After nitrogen was filled for at least 1 minute, then a rhenium-188 solution (10 mCi/0.5 ml) was added, and after nitrogen was filled for at least 1 minute, the reaction was carried out for 60 minutes at 95° C. After the reaction ended, the mixture was cooled after 10-minute standing. After the pH value of the solution was adjusted to 5.5 with 1 N NaOH, the nanoparticle marking rhenium-188 of the present invention was obtained.

Figure 3A:
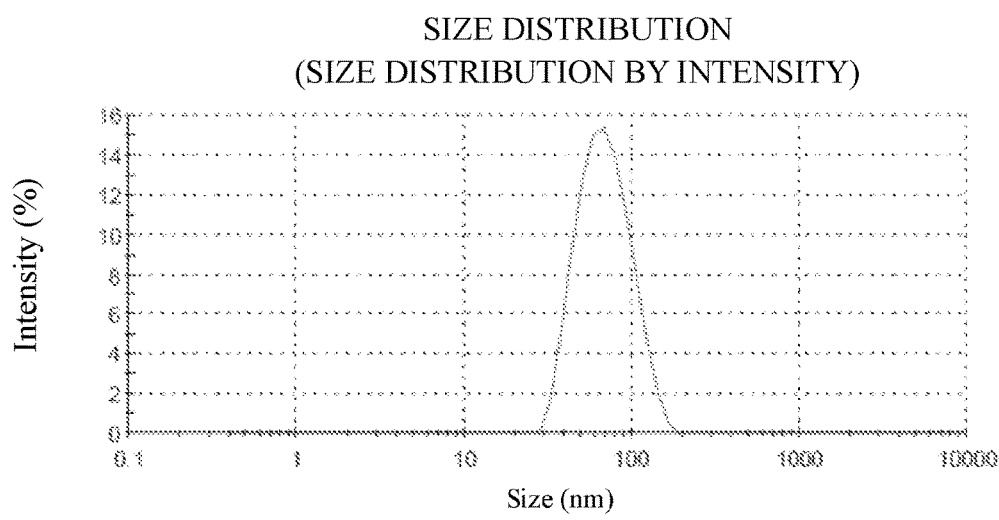
FIG. 3A is a graph showing the particle size distribution by intensity of PEG-HSA nanoparticle labelled with the rhenium-188 according to another embodiment of the present invention.
Figure 3B:
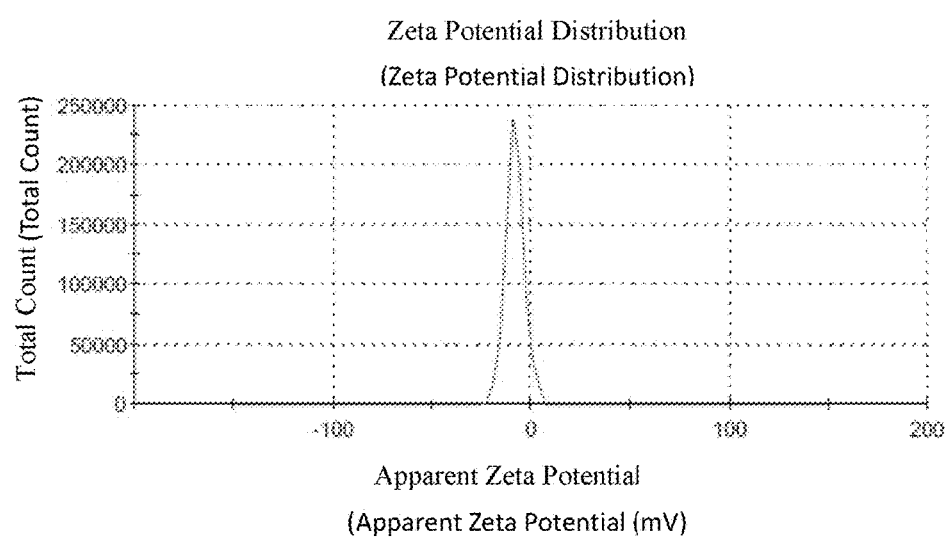
FIG. 3B shows results of analysis on surface potential of the nanoparticle marking a radioactive material of the present invention shown in FIG. 3A.

Particle size and potential of the nanoparticle marking rhenium-188 of the present invention were measured with radiochemical purity and a particle size analyzer, results showed that the chemical purity was 100%, the particle size was 64.5 nm, and the surface potential was −8.2 mV, and the results were respectively shown in FIG. 3A and FIG. 3B.

Specific examples disclosed above are not used to limit the claims of the present invention. Those of ordinary skill in the art can make modifications according to usual experience within the scope covered by the principle and spirit of the present invention, and thus the scope asserted in the present invention should be subject to that defined by the claims.

What is claimed is:

1. A method for manufacturing a nanoparticle, comprising:
   a) dissolving human serum albumin and polyethylene glycol having a maleimide functional group in a PBS solution and reacted for 20 hours to obtain a first mixture;
   b) dissolving the first mixture to a saline solution, and adding 0.05-0.2 N of sodium hydroxide;
   c) adding a methanol/ethanol mixture to precipitate the albumin;

d) adding a glutaraldehyde water solution under stirring for 12 hours;
e) obtaining the nanoparticle through ultracentrifugation;
f) dissolving the nanoparticle in a sodium chloride solution to obtain a second mixture;
g) adding a stannous chloride solution and a citric acid solution into the second mixture;
h) adding a rhenium-188 solution with nitrogen to obtain a nanoparticle that labeled with the rhenium-188.

2. The method according to claim 1, wherein step b) is completed to filter to obtain a filtering medium, and then step c) is performed.

* * * * *